United States Patent [19]

Kasahara et al.

[11] 4,419,445
[45] Dec. 6, 1983

[54] METHOD FOR DETERMINING THE ACTIVITY OF CHOLINESTERASES

[75] Inventors: Yasushi Kasahara, Tama; Yoshihiro Ashihara, Fuchu; Masami Sugiyama, Hachioji; Takahiro Harada, Ube, all of Japan

[73] Assignee: Fujizoki Pharmaceutical Co., Ltd., Tokyo, Japan

[21] Appl. No.: 360,723

[22] Filed: Mar. 22, 1982

[30] Foreign Application Priority Data

Apr. 8, 1981 [JP] Japan .................................. 56-51708

[51] Int. Cl.$^3$ ........................... C12Q 1/46; C12Q 1/26
[52] U.S. Cl. ......................................... 435/20; 435/25
[58] Field of Search ................................... 435/20, 25

[56] References Cited

U.S. PATENT DOCUMENTS 3,959,351 5/1976 Day et al. ............................ 424/308
4,271,310 6/1981 Watanabe et al. .................. 424/309

FOREIGN PATENT DOCUMENTS 63021 10/1982 European Pat. Off. ............. 435/20

Primary Examiner—Esther M. Kepplinger
Attorney, Agent, or Firm—Flynn, Thiel, Boutell & Tanis

[57] ABSTRACT

A method for determining the activity of cholinesterase comprising the steps of:
    mixing a solution containing p-methoxybenzoate demethylmonooxygenase, nicotinamide adenine dinucleotide reduced form (NADH) and p-methoxybenzoyl choline cation having the following formula:

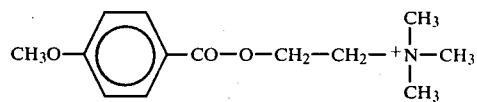

with a liquid containing cholinesterase, measuring the decrease in absorbance of light by NADH, which is based on a consumption of NADH, and calculating the activity of cholinesterase therefrom.

3 Claims, No Drawings

METHOD FOR DETERMINING THE ACTIVITY OF CHOLINESTERASES

BACKGROUND OF THE INVENTION

The present invention relates to a method for determining the activity of cholinesterases.

There are known two kinds of cholinesterase, namely, (1) true cholinesterase, and (2) pseudocholinesterase. True cholinesterase can be found in human red blood cells and human nerve tissues. Pseudocholinesterase can be found in human blood serum and in the human pancreas. Both kinds of cholinesterase decompose (hydrolyze) acylcholines (e.g., acetylcholine) to choline and an acid (e.g., choline and acetic acid). The present invention is effective for determining the activity of both kinds of cholinesterase. The term, cholinesterase, used hereinafter, includes both true and pseudocholinesterase.

When a person suffers from hepatic disease or anemia, the amount of cholinesterase in the blood decreases. When a person suffers from nephrosis, diabetes mellitus or a disease of the nervous system, the amount of cholinesterase in the blood increases. A diagnostic indication of the existence of the diseases mentioned above can be made by measuring the level of cholinesterase in the blood. The accurate determination of the activity of cholinesterase contained in the blood serum is therefore significant from physiological and clinical viewpoints. As conventional methods for making that determination, there are known (1) the Takahashi and Shibata method, in which acetyl choline is used as a substrate and the variation of the pH caused by decomposition thereof is measured, and (2) a method in which benzoylcholine is used as a substrate, choline liberated from the benzoylcholine is oxidized with choline oxidase to liberate hydrogen peroxide ($H_2O_2$), the hydrogen peroxide is subjected to reaction with phenol and 4-aminoantipyrine with peroxidase to produce quinonimine dye, and the concentration of the quinonimine dye produced is colorimetrically measured.

However, such conventional methods have disadvantages. The method (1) requires complicated steps and the method (2) does not give good measurement results with high precision.

It is an object of the present invention to provide a simple method for determining the activity of cholinesterase.

SUMMARY OF THE INVENTION

The principle of the method of the present invention is as follows:

p-methoxybenzoyl choline substance that provides a cation having the following formula is used as a synthetic substrate:

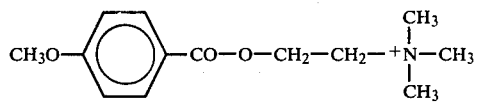

A liquid, such as a human blood serum, containing cholinesterase, is added to a solution containing a p-methoxybenzoate demethylmonooxygenase, reduced nicotinamide adenine dinucleotide (conventionally and hereinafter referred to as NADH) and the substance providing the p-methoxybenzoyl choline cation, as defined above. p-methoxybenzoic acid is produced from p-methoxybenzoyl choline by the action of cholinesterase. The p-methoxybenzoic acid is changed to p-hydroxybenzoic acid by the action of the p-methoxybenzoate demethylmonooxygenase, in the presence of NADH. The NADH consumption is measured by measuring the decrease in absorbance of light by NADH. The activity of cholinesterase is determined by calculation from the decrease in absorbance of light by NADH.

The synthetic substrate which is used in the present invention, namely, a substance providing the p-methoxybenzoyl choline cation, can be synthesized as follows:

25 g of thionyl chloride was added to 5 g of p-methoxybenzoic acid. After the temperature of the mixture was kept at 70° C. for 6 hours under reflux, the mixture was heated under reduced pressure to remove unchanged thionyl chloride. The residue was dissolved in benzene, and after the solution was heated to be condensed, it was cooled to produce precipitate. The precipitate was recrystallized with benzene to obtain p-methoxybenzoyl chloride. 10 mmol of choline chloride was added to 10 mmol of p-methoxybenzoyl chloride. The temperature of the mixture was kept at 120° C. for 5 hours. The residue was separated and purified by subjecting to silica gel chromatography to obtain p-methoxybenzoyl choline chloride.

EXAMPLE

The activity of cholinesterase contained in a human blood serum sample was determined.

5 μl of human blood serum was added to 1 ml of a solution (pH 7.5) containing 0.1 mM of p-methoxybenzoyl choline chloride, 3 U (enzyme activity units) of p-methoxybenzoate demethylmonooxygenase, 0.2 mM of NADH and 100 mM of phosphate buffer. The decrease of the absorbance by the solution was measured at a light wavelength of 340 nm, at a temperature of 30° C., during the course of the reaction. In the measurement, a reaction rate analyzer (LKB 2086 made and sold by Clinicon Co., Sweden) was employed. The time lag was 5 seconds and the reaction time was 5 minutes. The enzyme activity unit (U) of cholinesterase is automatically printed out in the analyzer. The activity calculations were made according to the following formula:

$$U = \frac{\text{Decrease in absorbance at 340 nm}}{\text{Reaction time (5 min)}} \times$$

$$\frac{1}{\text{Molecular extinction coefficient } (\epsilon)} \times \frac{1}{\text{Light-path length (cm)}} \times \frac{1.005}{0.005} \times 10^3$$

$\epsilon = 6.22 \times 10^3$ (Molecular extinction coefficient of NADH)

The results of the measurements, repeated 30 times, were as follows:

Activity unit (U) of cholinesterase = 160~320 (nmol/ml/min)

Coefficient of variation (CV) = 2.67%

We claim:

1. A method for determining the activity of cholinesterase, comprising the steps of:

mixing a liquid containing cholinesterase with a solution containing p-methoxybenzoate demethylmonooxygenase, reduced nicotinamide adenine dinucleotide (NADH) and p-methoxybenzoyl choline cation having the formula:

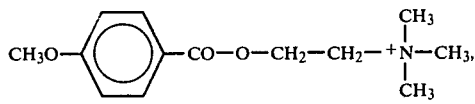

under conditions effective to transform said p-methoxybenzoyl choline first to the corresponding p-methoxybenzoic acid and then to p-hydroxybenzoic acid and to convert said NADH to NAD+, and measuring the decrease in absorbance of light caused by NADH, which decrease is caused by conversion of NADH to NAD+.

2. A method according to claim 1, wherein the enzyme activity (U) of cholinesterase is calculated based on the decrease in absorbance of light of said NADH.

3. A method according to claim 2, wherein said p-methoxybenzoyl choline cation is provided by p-methoxybenzoyl choline chloride.

* * * * *